US008877256B2

(12) United States Patent
Dudnik et al.

(10) Patent No.: US 8,877,256 B2
(45) Date of Patent: Nov. 4, 2014

(54) ANTIMICROBIAL PHOTO-STABLE COATING COMPOSITION

(75) Inventors: Vyacheslav Dudnik, Mississauga (CA); Yakeemovich Natali, Mississauga (CA); Valerio DiTizio, Toronto (CA); Frank DiCosmo, Richmond Hill (CA)

(73) Assignee: Covalon Technologies Ltd., Ontario (CA)

( * ) Notice: Subject to any disclaimer, the term of this patent is extended or adjusted under 35 U.S.C. 154(b) by 558 days.

(21) Appl. No.: 12/183,426

(22) Filed: Jul. 31, 2008

(65) Prior Publication Data

US 2009/0035388 A1 Feb. 5, 2009

Related U.S. Application Data

(60) Provisional application No. 60/935,259, filed on Aug. 2, 2007.

(51) Int. Cl.
| | |
|---|---|
| A61K 33/38 | (2006.01) |
| A61K 31/555 | (2006.01) |
| A61L 31/10 | (2006.01) |
| A61L 15/18 | (2006.01) |
| A01N 25/34 | (2006.01) |
| A61K 31/785 | (2006.01) |
| A01N 59/16 | (2006.01) |
| A61L 15/46 | (2006.01) |
| A61L 27/30 | (2006.01) |
| A61L 27/54 | (2006.01) |
| A61L 29/10 | (2006.01) |
| A61L 29/16 | (2006.01) |
| A61L 31/08 | (2006.01) |
| A61L 31/16 | (2006.01) |
| C08J 7/06 | (2006.01) |
| C08J 7/18 | (2006.01) |
| C09D 5/14 | (2006.01) |

(52) U.S. Cl.
CPC ................ *A61L 15/18* (2013.01); *A61K 33/38* (2013.01); *A01N 25/34* (2013.01); *A61K 31/785* (2013.01); *A01N 59/16* (2013.01); *A61L 15/46* (2013.01); *A61L 27/306* (2013.01); *A61L 27/54* (2013.01); *A61L 29/106* (2013.01); *A61L 29/16* (2013.01); *A61L 31/088* (2013.01); *A61L 31/16* (2013.01); *C08J 7/06* (2013.01); *C08J 7/18* (2013.01); *C09D 5/14* (2013.01); *A61L 2300/104* (2013.01); *A61L 2300/404* (2013.01); *A61L 2300/80* (2013.01); *C08J 2383/04* (2013.01)

USPC ........... 424/618; 514/184; 514/495; 427/2.24

(58) Field of Classification Search
None
See application file for complete search history.

(56) References Cited

U.S. PATENT DOCUMENTS

| 4,646,730 | A | 3/1987 | Schonfeld et al. |
|---|---|---|---|
| 4,906,466 | A | 3/1990 | Edwards et al. |
| 5,413,788 | A | 5/1995 | Edwards et al. |
| 5,788,687 | A | 8/1998 | Batich et al. |
| 6,468,521 | B1 | 10/2002 | Pedersen et al. |
| 6,669,981 | B2 | 12/2003 | Parsons et al. |
| 6,808,738 | B2 | 10/2004 | DiTizio et al. |
| 2002/0161065 | A1* | 10/2002 | DiTizio et al. .................... 522/1 |
| 2005/0131356 | A1* | 6/2005 | Ash et al. ....................... 604/265 |

FOREIGN PATENT DOCUMENTS

| CA | 2 263 473 | 2/1998 |
|---|---|---|
| CA | 2 615 654 | 4/2007 |
| JP | 2000-256365 | 9/2000 |
| JP | 2001-335405 | 12/2001 |
| WO | WO 00/09173 A1 | 2/2000 |
| WO | WO 2005/049101 A1 | 6/2005 |

OTHER PUBLICATIONS

JP 2001-335405 Machine translation, translated Jul. 8, 2010, pp. 1-15.*
Nomiya, K., et al. "Synthesis and Characterization of Water-Soluble Silver(I) Complexes with $_L$-Histidine ($H_2$his) and (S)-(−)-2-Pyrrolidone-5-carboxylic Acid ($H_2$pyrrld) Showing a Wide Spectrum of Effective Antibacterial and Antifungal Activities. Crystal Structures of Chiral Helical Polymers $[Ag(Hhis)]_n$ and $\{[Ag(Hpyrrld)]_2\}_n$ in the Solid State" Inorganic Chemistry, vol. 39, (2000) pp. 3301-3311.
International Search Report for PCT/CA2008/001396 dated Dec. 18, 2008.
Lindgren, Sofia et al., "Design of a Small Diameter Fibre Optical Probe for Interstitial Chromophore Concentration Measurements" Master's Thesis, Lund Reports on Atomic Physics, Jan. 2007, LRAP-372 Lund, pp. 1-68.
Supplementary European Search Report for EP 08 78 3307 dated Jul. 18, 2011.

* cited by examiner

*Primary Examiner* — Ernst V Arnold
*Assistant Examiner* — Kyung Sook Chang
(74) *Attorney, Agent, or Firm* — Knobbe Martens Olson & Bear LLP

(57) ABSTRACT

The invention is an antimicrobial photo-stable coating composition that deters photo-induced discoloration, does not stain tissue and can be applied to the surface of a variety of medical materials. The composition comprises in an aspect silver-PCA complex and dye.

34 Claims, No Drawings

ANTIMICROBIAL PHOTO-STABLE COATING COMPOSITION

CROSS REFERENCE OF RELATED APPLICATIONS

This application claims the benefit of priority to U.S. Provisional Patent Application No. 60/935,259, filed Aug. 2, 2007, the disclosure is hereby expressly incorporated by reference in its entirety.

BACKGROUND OF THE INVENTION

1. Field of the Invention

The invention is directed to a photo-stable coating. In particular, the invention is an antimicrobial photo-stable composition used for coating a variety of medical materials. The invention also contemplates methods of making such composition, methods of forming coatings on medical materials and medical materials coated with the coating composition.

2. Description of the Related Art

Throughout this application, various references are cited in parentheses to describe more fully the state of the art to which this invention pertains. The disclosure of these references are hereby incorporated by reference into the present disclosure.

Anti-microbial agent(s) such as acetohydroxamic acid and magnesium ammonium phosphate hexahydrate have been added to a surface polymer coating as is disclosed for example in U.S. Pat. No. 5,788,687.

Silver is known to have general anti-microbial properties directed against a wide range of bacteria and fungi and has been used for many years in clinical settings and on medical devices which include coatings for catheters, cuffs, orthopedic implants, sutures, dental amalgams and wound dressings. Silver has been demonstrated to reduce the incidence of infection associated with the use of such devices. Silver alloy and silver oxide have been used to coat urinary catheters and are somewhat effective in preventing urinary tract infections.

The general use of silver as a prophylactic against infection has not found widespread application because of problems associated with the inadequate coating of device surfaces. Such problems include: poor solubility of metallic silver and silver oxides; short half-life; rapid binding of silver ions; inactivation by proteins; light-mediated inactivation and discoloration; and slow release of silver ions from the metallic complex. While not subscribing to any particular theory, colorless cationic silver may be photoreduced to metallic silver with subsequent dark discoloration. The ensuing discoloration of the ionic silver when coated onto medical devices results in undesirable coloration of the material or surface of the device.

U.S. Pat. No. 4,646,730 discloses polyvinylpyrrolidone (PVP)/silver sulfadiazine hydrogel dressings, where the gel is formed by utilizing electron beam irradiation to crosslink the PVP. Photo-stabilization of the silver component is accomplished by adding magnesium tri-silicate to the gel and by also adding hydrogen peroxide and/or polyacrylic acid.

U.S. Pat. No. 6,468,521 discloses a stabilized silver composition in which the silver compound is a complex with a primary, secondary or tertiary amine and the complex is associated with a hydrophilic polymer.

U.S. Pat. Nos. 4,906,466 and 5,413,788 disclose antimicrobial silver compositions in which photo-stability is enhanced by use of titanium oxide.

U.S. Pat. No. 6,669,981 discloses methods for enhancing the photo-stability of silver comprising an organic solution containing silver where the silver is subsequently photo-stabilized by treatment with ammonia, ammonium salts, thiosulfates, chlorides and/or peroxides.

Nomiya et al. (Inorganic Chemistry: 39:3301-3311, 2000) disclose the synthesis of water-soluble silver-pyrrolidone carboxylic acid (silver-PCA) complexes with antimicrobial activity. The material so produced shows discoloration caused by photoreduction of the silver-PCA complex.

JP 2001335405 and JP 2000256365 describe compounds that form a photostable complex with silver. The most effective was a silver-2-pyrrolidone-5-carboxylic acid complex (silver-PCA). However, photo-reduction and discoloration of the complex remains a problem.

There remains a need to develop a hydrophilic silver-complex that deters photo-induced discoloration of the silver-PCA complex on the surface of medical devices such as catheters, wound dressings and the like.

SUMMARY OF THE INVENTION

The present invention is an antimicrobial photo-stable coating composition. The coating composition comprises a complexed silver salt and dye. In an aspect, the coating composition comprises silver, pyrrolidone carboxylic acid (PCA) and dye. The coating composition of the invention can also be used on medical devices that have been provided with a hydrophilic coating and may further be lubricious.

The coating composition of the invention provides photo-stability to the silver ions contained therein and is hydrophilic and antimicrobial. As such, the hydrophilic silver-complex of the composition deters photo-induced discoloration, does not substantially stain tissue and can be applied to the surface of a variety of medical materials such as catheters, wound dressings and the like, and can be used as an adjunct in the formulation of hydrogels and hydrophilic coatings.

According to an aspect of the present invention is an antimicrobial photo-stable coating composition that deters photo-induced discoloration, does not substantially stain tissue and can be applied to the surface of a variety of medical materials.

According to a further aspect of the present invention is an antimicrobial photo-stable composition comprising silver, dye and a molecule having a basic nitrogen atom for complexing with the silver. In aspects of the invention, the silver is complexed with the nitrogen atom-containing molecule within the composition and then dye is added thereto.

According to a further aspect of the present invention is an antimicrobial photo-stable composition comprising silver, pyrrolidone carboxylic acid (PCA) and dye. In aspects of the invention, the silver is complexed with the PCA within the composition and then silver is added thereto.

According to a further aspect of the present invention is an antimicrobial photo-stable composition comprising silver, pyrrolidone carboxylic acid (PCA) and one or more amino acids. In aspects of the invention, the silver is complexed with the amino acid(s) and the PCA within the composition and then silver is added thereto. In further aspects the amino acid is histidine.

According to another aspect of the invention is an antimicrobial photo-stable coating composition comprising complexed silver, wherein said composition deters photo-induced discoloration, does not substantially stain tissue and can be applied to the surface of a variety of medical materials.

In aspects, the composition comprises complexed silver and dye.

In aspects, the complexed silver comprises silver salt complexed to a molecule with a basic nitrogen atom to protect said silver from subsequent oxidation/reduction reactions. In aspects, the molecule is an amino-containing molecule. In further aspects of the invention the molecule is selected from the group consisting of ammonia, glycine, glutamic acid, tris(hydroxymethyl)aminomethane, polyethyleneimine, pyrrolidone carboxylic acid (PCA) and mixtures thereof.

In further aspects of the invention, the composition additionally comprises one or more amino acid.

In still further aspects of the invention the silver is complexed with the PCA or with the amino acid or with both the PCA/amino acid within said composition.

According to yet a further aspect of the present invention is an antimicrobial photo-stable composition comprising silver, one or more amino acids and dye. In aspects of the invention, the silver is complexed with the one or more amino acids within the composition and then silver is added thereto. In aspects, the amino acid is histidine.

According to another aspect of the present invention is an antimicrobial photo-stable coating composition that deters photo-induced discoloration, does not stain tissue and can be applied to the surface of a variety of medical materials, said composition comprising silver-PCA complex and dye(s).

According to still another aspect of the present invention is a method of making an antimicrobial photo-stable coating composition, said method comprising;
  forming a dry complex of silver-PCA; and
  adding dye and distilled water.

According to another aspect of the present invention is a method for making an antimicrobial photo-stable coating composition, said method comprising;
  (a) admixing a silver salt with PCA and lyophilizing to form a dry powder;
  (b) adding (a) to a dye solution.

According to another aspect of the present invention is a method for making an antimicrobial photo-stable coated medical material, said method comprising applying an antimicrobial photo-stable composition comprising silver, pyrrolidone carboxylic acid (PCA) and dye to said medical material. In aspects after applying the composition, the medical material is then dried.

According to yet another aspect of the present invention is a medical material coated with an antimicrobial photo-stable coating composition. In aspects, the composition comprises a silver-PCA complex and silver. In further aspects, the medical material has a hydrophilic coating to which the antimicrobial photo-stable coating composition of the invention is applied thereon. The hydrophilic coating also makes the medical material lubricious.

According to still another aspect of the present invention is a polymeric medical device having a hydrophilic coating made by the method comprising:
  incubating a photo-initiator-coated silicone material provided as a device selected from the group consisting of implants, catheters, stents, wound dressings, cardiac valves, tubings, pins and clips with an aqueous monomer solution capable of free radical polymerization and selected from the group consisting of acrylic acid, methacrylic acid, 2-carboxyethyl acrylate, 4-vinylbenzoic acid, itaconic acid, and mixtures thereof, wherein the photo-initiator Is selected from the group consisting of p-benzoyl tert-butylperbenzoate, benzophenone, tert-butylperoxybenzoate, 2,2-dimethoxy-2-phenyl-acetophenone, benzil ketals, benzoins and their derivatives and mixtures thereof;
  exposing the incubating material to ultraviolet (UV) light creating a modified surface on said material; and
  washing and drying said material with said modified surface, wherein said device is further coated or impregnated with an antimicrobial photo-stable coating composition.

In aspects, the photo-stable coating composition comprises silver-PCA and dye.

According to another aspect of the present invention is a method for making an antimicrobial photo-stable coated medical material, said method comprising;
  (a) admixing a silver salt with PCA and lyophilizing to form a dry powder;
  (b) adding (a) to a dye solution;
  (c) dipping a medical material into (b) for a desired time; and
  (d) drying said medical material.

According to yet another aspect of the present invention is a polymeric composite comprising a photo-stable hydrophilic silver-PCA-dye coated-surface wherein said polymeric composite is lubricious and has antimicrobial properties.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DETAILED DESCRIPTION OF THE INVENTION

The invention is a novel antimicrobial and photo-stable coating composition for medical materials. It is now demonstrated that complexed silver treated with a solution of a dye, protects the silver ion from undesirable photo-reduction. As a result, photo-induced discoloration of coated medical materials does not occur. The coating also does not stain tissue. These advantages make the coating composition of the invention suitable for use on a variety of different types of medical materials.

In an embodiment of the invention, the silver is complexed with any molecule with a basic nitrogen atom that provides some level of protection from subsequent oxidation/reduction reactions that would lead to discoloration. In aspects, the molecule is an amino-containing molecule. In aspects, the molecule is selected from, but not limited to, ammonia, glycine, glutamic acid, tris(hydroxymethyl)aminomethane, polyethyleneimine, pyrrolidone carboxylic acid (PCA) and mixtures thereof The coating composition of the invention comprises in one aspect silver ions that are complexed with pyrrolidone carboxylic acid (silver-PCA). This complex may be synthesized and isolated as silver salt white powder. The complex concentration in the solution may be in the range from about 1 to about 20 mM. As the maximum solubility of silver-PCA in water is about 300 mM it is understood by one of skill in the art that the complex concentration may vary somewhat from the 1 to about 20 mM as desired. In some aspects of the invention, about 5 mM of the complex is desired to obtain desirable antimicrobial effects. In other aspects, 1 mole of silver nitrate per 2 moles of PCA provides desirable results; however, other ratios could be used to obtain the silver-PCA complex. It is understood that the concentration of the complex in the solution is similar to that taught for PCA for any of the desired molecules used that bind and protect the silver as is described herein.

In another aspect of the present invention the coating composition comprises silver ions that are complexed with an amino acid or a combination of amino acids and synthesized as silver salt white powder. In one aspect the amino acid is histidine, however, it is understood by one of skill in the art that any amino acid can be used or any combination of amino acids as is known to one of skill in the art. For example suitable amino acids for use in the composition of the invention may be selected from alanine, arginine, asparagine, aspartate, cysteine, glutamate, glutamine, glycine, histidine, isoleucine, leucine, lysine, methionine, phenylalanine, praline, serine, threonine, tryptophan, tyrosine, valine and combinations thereof The amount of amino acid to use in the composition with silver is that taught for PCA described above.

Still in another aspect of the invention a combination of the molecule containing a basic nitrogen atom to bind and complex with silver (e.g. ammonia, glycine, glutamic acid, tris (hydroxymethyl)aminomethane, polyethyleneimine, pyrrolidone carboxylic acid (PCA) and mixtures thereof) and amino acid(s) may be used to complex with the silver as is understood by one of skill in the art. The amount of amino acid(s) and molecule together would be used in amounts as is taught herein for PCA.

Silver cations may be provided from soluble silver salts, such as but not limited to silver nitrate, silver acetate, silver lactate and mixtures thereof, and form a complex with PCA in solution. The silver salts concentrations are in the range from about 1 mM to about 20 mM, and the PCA and/or amino acid concentration should be about twice the silver salt concentration for the solution used to prepare the solid silver/PCA or silver/amino acid or silver/amino acid and PCA complex. The dye is added in concentration from about 0.02 mM to about 2 mM in the final solution containing the silver complex.

The dye for use in the present invention is any cationic triarylmethane dye such as but not limited to Brilliant Green, Malachite Green, Methylene Blue, Ethyl Violet, Crystal Violet, Victoria Blue R, Victoria Blue B and Victoria Pure Blue BO and mixtures thereof, which are commercially available from Sigma-Aldrich, U.S.A. In aspects of the invention the dye used in the composition is Brilliant Green as used to exemplify one non-limiting embodiment of the invention. The dye molecules are added to the silver-PCA complex (or amino acid or amino acid and PCA complex) to absorb light in the wavelength range of about 550-680 nm and about 380-450 nm ranges and protect the silver ion complex from undesirable chemical reduction and consequent color changes.

The coating composition of the invention is made generally in one aspect by admixing the silver source with the PCA to form a complex that is then dried to form a silver salt powder. The same is done for amino acid or PCA and amino acid. To this is added a suitable dye solution. Any desired medical material is then dipped into, or the composition applied thereon as desired for a time sufficient to provide a coating. For example, the medical material may be dipped into the composition for seconds up to several minutes. Furthermore, the medical material can be dipped into the composition or the composition otherwise applied to the medical material such as by spraying for a non-limiting example. It is also within the scope of the invention to re-apply the coating composition to an already coated medical material substrate as desired as many times as desired. The coated medical material is then dried.

The coating composition of the invention can be used to treat a variety of medical materials, by treat it is meant to coat or impregnate if water absorbent materials are used to allow entry of the silver/PCA solution beyond surface regions as is understood by one of skill in the art. The medical materials may be selected from the group consisting of but not limited to hydrophilic materials and polymeric materials. Hydrophilic materials may be selected from the group consisting of but not limited to cotton gauze, polymer tubes such as urological catheters, wound drains, vascular grafts, endotracheal tubes, hemodialysis catheters, tissue coverings composed of proteins and carbohydrates and the like. The materials so coated are photo-stable which assists in maintaining the silver in the ionic state. Polymeric materials may be selected from the group consisting of medical devices selected from the group consisting of but not limited to catheters, wound drains, endotracheal tubes and other polymeric liquid flow conduits and polymeric sheet materials.

In further embodiments of the invention, the antimicrobial coating composition of the invention can be effectively used to coat polymeric medical devices treated with hydrophilic coatings as described in Applicant's U.S. Pat. No. 6,808,738 (the disclosure of which is incorporated herein by reference). Briefly, this patent describes that the surfaces of chemically inert polymers are permanently modified with a coating derived from a mixture of carboxylate-containing monomers and another vinyl co-monomer such as N-vinylacetamide, N-methylvinylacetamide, or methyl acrylate that can be made lubricious and then can be further endowed with a coating of the present invention. As such, the present invention provides for a polymeric composite that has a photostable hydrophilic silver-PCA-dye coated-surface possessing the characteristics of lubricity and antimicrobial properties.

The hydrophilic coating can be provided in a variety of configurations for different surfaces. The chemically inert polymers for use in the invention are those that are used and desirable to fabricate various types of in-dwelling devices. Examples of in-dwelling devices include but are not limited to implants, catheters, stents, vascular grafts, wound dressings, cardiac valves, pins, clamps, tubings and the like can be used in the practice of the invention. Polymers that can be surface modified according to the present invention include all polymeric substrates such as polyurethanes, polyamides, polyesters, polyethers, polyorganosiloxanes, polysulfones, polytetrafluoroethylene, polysiloxanes, carbohydrate materials including cellulose fibers such as cotton and chitosan; proteins, such as gelatin, collagen and the like, including combinations of polymers, carbohydrates and proteins.

In providing a hydrophilic coating on the surface of polymer materials such as liquid flow conduits, the method specifically involves adding hydrophilic co-polymers derived from vinyl monomers such as N-vinylacetamide, N-methylvinylacetamide, or methyl acrylate and carboxylic acid-containing monomers to the surface of inert substrates such as poly (dimethylsiloxane)-based polymers (silicone) through the use of long wavelength UV radiation (300-400 nm) and photoinitiators in a solution containing for example, tert-butylperoxybenzoate (TPB), and benzophenone (BP). Ratios of the photoinitiators can be 1:3; 1:2; 1:1; 2:1 and 3:1 with the preferred ratios 1:2; 1:1 and most preferred ratio being 1:1. In the preferred ratio of 1:1 of the photoinitiators, the concentration of the photoinitiators may be in the range of 25 mM-300 mM with the preferred range being 100-200 mM and the most preferred concentration being 200 mM at concentrations of 200 mM each (1:1). The method comprises an initial step of free radical-mediated graft polymerization of acrylic acid or various other acrylates and N-vinylacetamide on photo-initiator-coated polymer surfaces placed in aqueous solutions of monomer and exposed to UV light (365 nm). While UV light is used herein, it is readily appreciated by those familiar with the art that photo-initiators that absorb light and other wavelengths may be used. The photo-initiator is coated onto the surface of selected polymeric material by incubating the polymeric material in an ethanolic or methanolic solution of photo-initiator for a time sufficient that the photo-initiator will adhere to the polymeric surface. Any means of providing a photo-initiator coated polymeric material will suffice in the method of the present invention; this is followed by air-drying of the photo-initiator coated polymeric material. One skilled in the art can appreciate that the level of grafting may be controlled by adjustment of photo-initiator and monomer concentrations, as well as duration of irradiation. The variance of time of UV-irradiation can be in the range of 1-15 min with the preferred range being 2-10 min and the most preferred time of UV-irradiation is 6 min.

To summarize, the coating composition of the present invention can be provided on any type of medical material whether hydrophilic or polymeric. Furthermore, the medical material may already have a hydrophilic coating thereon as described herein and in Applicant's U.S. Pat. No. 6,808,738 (the disclosure of which is incorporated herein in its entirety).

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Silver-pyrrolidone Carboxylic Acid Complex (Ag-PCA complex) Synthesis

1. Make a 0.5 M $AgNO_3$ and 1 M PCA solution in distilled water
2. Titrate with $NH_4OH$ to pH=5.0
3. Pour into filtration funnel and filter through 0.45 μm filter paper.
4. Dry the white powder (preferably in dark).
5. Yield with respect to silver is 96%.

Example 2

Coating of Cotton Fibers

Cotton gauze bandages were coated with silver-PCA (Ag-PCA) complex and Brilliant Green. While certain durations are presented it is well known by those skilled in the art that an increase or decrease in the durations presented is sufficient to effect the embodiment of the present invention.

1. Silver-PCA complex and Brilliant Green: 2.4 g/L was dissolved in distilled water.
2. A cotton gauze was dipped into the solution for 1 second to 60 minutes, more preferably from 10 seconds to 10 minutes and most favorably from 1 min to 5 min.
3. Sample was rolled between two rubber rollers to press out non-absorbed solution.
4. Sample was washed 1 min in distilled water and pressed to remove excess water.
5. Sample dried at room temperature.

Example 3

Coating of silicone Foley Catheters

Process 1: The process is as described in Applicant's U.S. Pat. No. 6,808,738 (the disclosure of which is incorporated herein by reference in its entirety) for preparing a hydrophilic catheter surface. The catheters so produced may be coated with the silver-PCA-Brilliant Green solution effectively as an embodiment of the present application.

Process 2: Catheters are immersed in a solution of photo-initiator composed of 200 mM each of benzophenone and tert-butylperoxybenzoate for 1-10 min., preferably 1 min. The catheters are dried and immersed in a solution of 200 mM of acrylic acid and 50 mM of N-vinylacetamide with constant purging using nitrogen gas for 10 minutes; lesser times or more time allotted to this step is sufficient to demonstrate the embodiment of the invention. The samples in solution are irradiated with UV light (365 nm) for 5 minutes, less or more time is also effective, for surface grafting of the monomers to the silicone surfaces. The catheters are washed in ethanol, and transferred to a solution of Trizma base (pH 9; 10-100 mM). The catheters so treated are immersed in a solution of 2.5 mM silver acetate, 5 mM pyrrolidone carboxylic acid and 0.04 mM of Brilliant Green dye. Subsequently, the catheters are transferred to a solution of Trizma base (pH 8.5; 1-10 mM), and finally rinsed in de-ionized water and dried.

The residence time of catheters in each of the above solutions may be varied from 1-30 min, with 5-15 minutes being preferable and 12 minutes most preferable. However, it is easily understood by those familiar with the art that reducing or increasing the duration at each station are also embodiments of the present invention. Any cationic dye such as: Malachite Green, Methylene Blue, Ethyl Violet, Crystal Violet, Victoria Blue R, Victoria Blue B and Victoria Pure Blue BO, etc., and mixtures can also be used.

Example 4

Coating of Central Venous Catheters

Process 1: Catheters are immersed in a solution of photo-initiator composed of 200 mM each of benzophenone and tert-butylperoxybenzoate for 1-10 min., preferably 1 min. The catheters are dried and immersed in a solution of 200 mM of acrylic acid and 50 mM of N-vinylacetamide with constant purging using nitrogen gas for 10 minutes; lesser times or more time allotted to this step is sufficient to demonstrate the embodiment of the invention. The samples in solution are irradiated with UV light (365 nm) for 5 minutes, less or more time is also effective, for surface grafting of the monomers to the silicone surfaces. The catheters are washed in ethanol, and transferred to a solution of Trizma base (pH 9; 10-100 mM). The catheters so treated are immersed in a solution of 2.5 mM silver acetate, 5 mM pyrrolidone carboxylic acid and 0.04 mM of Brilliant Green dye. Subsequently, the catheters are transferred to a solution of Trizma base (pH 8.5; 1-10 mM), and finally rinsed in de-ionized water and dried.

Example 5

Coating of Peripherally-Inserted Central Catheters

Process 1: Catheters are immersed in a solution of photo-initiator composed of 200 mM each of benzophenone and tert-butylperoxybenzoate for 1-10 min., preferably 1 min. The catheters are dried and immersed in a solution of 300 mM of acrylic acid and 50 mM of methyl acrylate with constant purging using nitrogen gas for 6 minutes; lesser times or more time allotted to this step is sufficient to demonstrate the embodiment of the invention. The samples in solution are irradiated with UV light (365 nm) for 6 minutes, less or more time is also effective, for surface grafting of the monomers to the silicone surfaces. The catheters are washed in ethanol, and transferred to a solution of Trizma base (pH 9; 10-100 mM). The catheters so treated are immersed in a solution of 2.5 mM silver acetate, 2.5 mM pyrrolidone carboxylic acid and 0.04 mM of Crystal Violet dye for 3 min. Subsequently, the catheters are rinsed in de-ionized water and dried.

The residence time of catheters in each of the above solutions may be varied from 1-30 min, with 5-15 minutes being preferable and 12 minutes most preferable. However, it is easily understood by those familiar with the art that reducing or increasing the duration at each station are also embodiments of the present invention. Any cationic dye such as: Malachite Green, Methylene Blue, Ethyl Violet, Crystal Violet, Victoria Blue R, Victoria Blue B and Victoria Pure Blue BO, etc., and mixtures can also be used.

Although preferred embodiments of the invention have been described herein in detail, it will be understood by those skilled in the art that variations may be made thereto without departing from the spirit of the invention.

What is claimed is:

1. An antimicrobial photo-stable coating composition comprising complexed silver and dye, wherein said complexed silver comprises silver salt complexed to a molecule with a basic nitrogen atom to protect said silver from subsequent oxidation/reduction reactions, wherein said molecule is selected from the group consisting of ammonia, glycine, glutamic acid, tris(hydroxymethyl)aminomethane, polyethyleneimine, pyrrolidone carboxylic acid (PCA) and mixtures thereof, and wherein said dye absorbs light in the wavelength range of about 550-680 nm and about 380-450 nm and thereby deters photo-induced discoloration, and wherein said composition does not substantially stain tissue and can be applied to the surface of a variety of medical materials.

2. The composition of claim 1, wherein said composition additionally comprises one or more amino acids.

3. The composition of claim 2, wherein said silver is complexed with the PCA or with the amino acids or with both the PCA/amino acid within said composition.

4. The composition of claim 1, wherein said silver salt is present in an amount of about 1 mM to about 20 mM.

5. The composition of claim 4, wherein said PCA is present in about twice the amount of said silver salt.

6. The composition of claim 1, wherein said dye is present in an amount of about 0.02 mM to about 2 mM.

7. The composition of claim 4, wherein said silver salt is selected from the group consisting of silver nitrate, silver acetate, silver lactate and combinations thereof.

8. The composition of claim 3, wherein said amino acid is selected from the group consisting of alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine and combinations thereof.

9. The composition of claim 8, wherein said amino acid is histidine.

10. The composition of claim 1, wherein said dye is a cationic triarylmethane dye.

11. The composition of claim 1, wherein said dye is selected from the group consisting of Brilliant Green, Malachite Green, Methylene Blue, Ethyl Violet, Crystal Violet, Victoria Blue R, Victoria Blue B and Victoria Pure Blue BO and mixtures thereof.

12. A medical material coated or impregnated with the composition of claim 1.

13. The medical material of claim 12, wherein said medical material is a device selected from the group consisting of implants, catheters, stents, wound dressings, cardiac valves, tubings, pins and clips.

14. The medical material of claim 13, wherein said device has a hydrophilic coating thereon, prior to being coated or impregnated with said composition.

15. A polymeric medical device having a hydrophilic coating made by the method comprising:
incubating a photo-initiator-coated silicone material provided as a device selected from the group consisting of implants, catheters, stents, wound dressings, cardiac valves, tubings, pins and clips with an aqueous co-monomer solution capable of free radical polymerization and selected from the primary group consisting of acrylic acid, methacrylic acid, 2-carboxyethyl acrylate, 4-vinylbenzoic acid, itaconic acid, and mixtures thereof and a secondary group consisting of any vinyl monomer such as N-vinylacetamide, N-methylvinylacetamide, or methyl acrylate, wherein the photo-initiator Is selected from the group consisting of p-benzoyl tert-butylperbenzoate, benzophenone, tert-butylperoxybenzoate, 2,2-dimethoxy-2-phenyl-acetophenone, benzil ketals, benzoins and their derivatives and mixtures thereof;
exposing the incubating material to ultraviolet (UV) light creating a modified surface on said material; and
washing and drying said material with said modified surface, wherein said device is further coated or impregnated with an antimicrobial photo-stable coating composition comprising complexed silver and dye, wherein said complexed silver comprises silver salt complexed to a molecule with a basic nitrogen atom to protect said silver from subsequent oxidation/reduction reactions, wherein said molecule is selected from the group consisting of ammonia, glycine, glutamic acid, tris(hydroxymethyl)aminomethane, polyethyleneimine, pyrrolidone carboxylic acid (PCA) and mixtures thereof, and wherein said dye absorbs light in the wavelength range of about 550-680 nm and about 380-450 nm and thereby deters photo-induced discoloration.

16. A method of making said antimicrobial photo-stable coating composition of claim 1, said method comprising;
forming a dry complex of said silver-PCA; and
adding dye and distilled water to form a solution.

17. The method of claim 16, wherein said complex of silver-PCA is formed by admixing said silver salt with said PCA and lyophilizing to form a dry powder.

18. A medical material coated with said antimicrobial photo-stable coating composition of claim 3.

19. The medical material of claim 18, wherein said material is selected from the group consisting of hydrophilic materials and polymeric materials.

20. The medical material of claim 19, wherein hydrophilic materials are selected from the group consisting of cotton gauze, polymer tubes, wound drains, vascular grafts, endotracheal tubes, hemodialysis catheters, tissue coverings composed of proteins and carbohydrates.

21. The medical material of claim 20, wherein said polymer tube is a urological catheter.

22. The medical material of claim 19, wherein said polymeric material are medical devices selected from the group consisting of catheters, wound drains, endotracheal tubes and other polymeric liquid flow conduits and polymeric sheet materials.

23. A method for making said antimicrobial photo-stable coated medical material of claim 12, said method comprising;

(a) admixing said silver salt with said PCA and lyophilizing to form a dry powder;
(b) adding (a) to a dye solution;
(c) dipping a medical material into (b) for a desired time; and
(d) drying said medical material.

24. The method of claim 23, wherein said silver salt is present in an amount of about 1 mM to about 20 mM.

25. The method of claim 23, wherein said PCA is present in about twice the amount of said silver salt.

26. The method of claim 23, wherein said dye is present in an amount of about 0.02 mM to about 2 mM.

27. The method of claim 23, wherein said silver salt is selected from the group consisting of silver nitrate, silver acetate, silver lactate and combinations thereof 28. The method of claim 23, wherein said dye is a cationic triarylmethane dye.

29. The method of claim 28, wherein said dye is selected from the group consisting of Brilliant Green, Malachite Green, Methylene Blue, Ethyl Violet, Crystal Violet, Victoria Blue R, Victoria Blue B and Victoria Pure Blue BO and mixtures thereof.

30. The method of claim 23, wherein said medical material is selected from the group consisting of hydrophilic materials and polymeric materials.

31. The method of claim 30, wherein hydrophilic materials are selected from the group consisting of cotton gauze, polymer tubes, wound drains, vascular grafts, endotracheal tubes, hemodialysis catheters, tissue coverings composed of proteins and carbohydrates and the like.

32. The method of claim 31, wherein said polymer tube is a urological catheter.

33. The method of claim 31, wherein said polymeric material are medical devices selected from the group consisting of catheters, wound drains, endotracheal tubes and other polymeric liquid flow conduits and polymeric sheet materials.

34. The device of claim 15, wherein the vinyl monomer is selected from the group consisting of N-vinylacetamide, N-methylvinylacetamide and methyl acrylate.

* * * * *